United States Patent [19]

Silvestrini

[11] Patent Number: 5,234,456
[45] Date of Patent: Aug. 10, 1993

[54] HYDROPHILIC STENT

[75] Inventor: Thomas A. Silvestrini, East Lyme, Conn.

[73] Assignee: Pfizer Hospital Products Group, Inc., New York, N.Y.

[21] Appl. No.: 883,241

[22] Filed: May 7, 1992

Related U.S. Application Data

[63] Continuation of Ser. No. 477,264, Feb. 8, 1990, abandoned.

[51] Int. Cl.$^5$ ............................................. A61M 29/02
[52] U.S. Cl. ....................................... 606/194; 623/1; 604/96
[58] Field of Search .................... 604/8, 96, 101, 264, 604/265, 280, 281, 285; 606/192, 194, 198, 108; 623/1, 12

[56] References Cited

U.S. PATENT DOCUMENTS

| | | | |
|---|---|---|---|
| 1,887,526 | 11/1931 | Spielberg et al. | 604/287 |
| 4,237,893 | 12/1980 | Michaels | 606/193 |
| 4,258,704 | 3/1981 | Hill | 600/32 |
| 4,434,797 | 3/1984 | Silander | 606/191 |
| 4,503,569 | 3/1985 | Dotter | 623/1 |
| 4,610,688 | 9/1986 | Silvestrini et al. | 623/12 X |
| 4,655,771 | 4/1987 | Wallsten | 604/281 X |
| 4,733,665 | 3/1988 | Palmaz | 604/96 X |
| 4,739,762 | 4/1988 | Palmaz | 604/96 X |
| 4,785,059 | 11/1988 | Fydelor et al. | 525/301 |
| 4,911,691 | 3/1990 | Aniuk et al. | 604/164 |
| 4,994,047 | 2/1991 | Walker et al. | 604/264 |

FOREIGN PATENT DOCUMENTS

1069826  1/1984  U.S.S.R.

*Primary Examiner*—C. Fred Rosenbaum
*Assistant Examiner*—Corrine Maglione
*Attorney, Agent, or Firm*—Peter C. Richardson; Lawrence C. Akers; Eric M. Lee

[57] ABSTRACT

A stent for placement within a body lumen and comprising a wall structure wherein at least a portion thereof is a hollow wall. The hollow wall has disposed therein a hydrophilic material which can be in the form of a gel, for example, which swells upon introduction of a liquid into the hollow wall to thereby achieve inflation thereof. The hollow wall is fabricated of a semi-permeable membrane whereby fluid from tissues surrounding the stent at the site of placement can pass through the membrane and swell the hydrophilic material to thereby inflate the hollow wall. A drug can be disposed with the hydrophilic material for release through the membrane at the site of stent placement. The entire wall structure of the stent can be a hollow wall, or the wall structure can incorporate both hollow and non-hollow wall portions such as hollow and solid fibers which are braided, woven or wound together.

12 Claims, 1 Drawing Sheet

HYDROPHILIC STENT

This is a continuation of application Ser. No. 477,264, filed on Feb. 8, 1990, now abandoned.

BACKGROUND OF THE INVENTION

This invention relates generally to stents employed to maintain in an open configuration a body lumen such as a duct or vessel, and in particular to a stent having a hollow and inflatable wall.

The employment of stents to maintain otherwise closed or occluded body lumens such as ducts or vessels, for example, in an open configuration is a well-recognized treatment procedure. Current commonly used stents include self-expanding stents as described in U.S. Pat. No. 4,655,771, for example, and stents which are expanded at the lumen site by a balloon which is inflated within the stent. In either case, the stents are usually constructed of metal, and therefore generally possess a degree of stiffness and a minimal pliability.

It is therefore a primary object of the present invention to provide a stent having a wall which is soft and pliable upon insertion, but which has the capability to provide the proper magnitude of stiffness and rigidity after placement at the site of treatment. Another object of the present invention is to provide such a stent wherein at least a portion of its wall structure is a hollow and inflatable wall fabricated of a semi-permeable membrane. Yet another object of the present invention is to provide such a stent wherein the hollow wall has disposed therein a hydrophilic material capable of absorbing a liquid to thereby increase the volume of the material and consequently inflate the wall. Still another object of the present invention is to provide such a stent wherein the hydrophilic material has therewith a drug. These and other objects of the invention will become apparent throughout the following description.

SUMMARY OF THE INVENTION

The present invention is a stent for placement within a body lumen and comprising a wall structure wherein at least a portion thereof is a hollow wall. The hollow wall has disposed therein a hydrophilic material which can be in the form of a gel, for example, which swells upon introduction of a liquid into the hollow wall to thereby achieve inflation thereof. The hollow wall with hydrophilic material therein is fabricated of a semi-permeable membrane whereby fluid from tissues surrounding the stent at the site of placement can pass through the membrane and swell the hydrophilic material to thereby inflate the wall. A therapeutic drug can be included with the hydrophilic material for release through the membrane at the site of stent placement. Examples of body lumens wherein a stent of the present invention can be employed include, but are not necessarily limited to, arteries, veins, urethral and ureteral ducts, biliary, hepatic and pancreatic ducts, bronchial, esophageal and bowel sections, sperm and fallopian ducts, eustachian tubes and lacrimal ducts. The entire wall structure of the stent can be a hollow wall, or the wall structure can incorporate both hollow and non-hollow portions such as hollow and solid fibers which are held together by being braided, woven or wound together.

The present invention provides a stent which, when placed and subsequently inflated, supports a lumen, yet, because the stent can be delivered to its site in a non-inflated configuration, also provides consequent compact size during delivery to enhance placement within a lumen.

BRIEF DESCRIPTION OF THE DRAWINGS

Presently preferred embodiments of the invention are illustrated in the accompanying drawings in which.

DETAILED DESCRIPTION OF PREFERRED EMBODIMENTS

Figure 1:
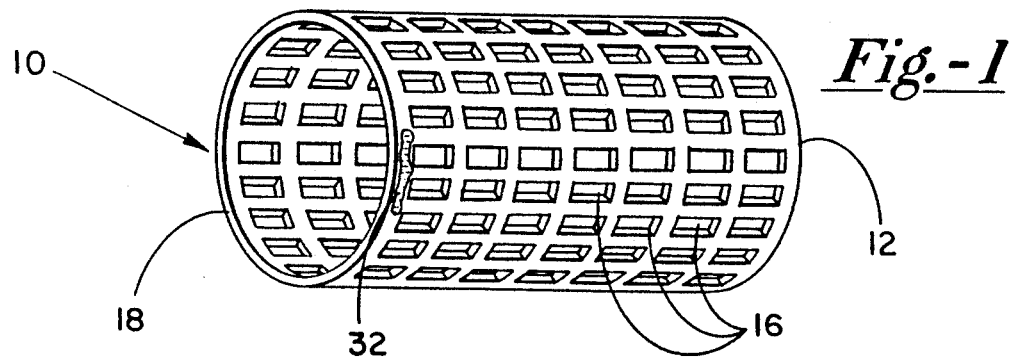
FIG. 1 is a perspective view of a tubular stent, partially in section, whose entire wall structure is a hollow wall comprising an inflatable balloon.

Referring to FIG. 1, a tubular stent 10 for placement within a body lumen is illustrated. The entire wall structure of the stent 10 is a hollow and inflatable wall 12 comprising a balloon 18 having a plurality of radial openings 16 therethrough to facilitate tissue ingrowth when the stent 10 is in place within a body lumen. The wall 12 is fabricated of a semi-permeable membrane whose construction is exemplified by polymers that can be formed into semi-permeable membranes as known in the art and capable of withstanding suitable inflation pressure. Non-limiting examples include polyamides, polyesters, polyurethanes, and ethylene vinyl alcohol. The stent 10 has disposed within its hollow wall 12 a hydrophilic material 32 which is capable of absorbing or attracting a liquid via osmotic dilution to thereby increase the volume of or pressure exerted by material 32. This hydrophilic material 32 can be any bio-compatible agent that will drive an osmotic pressure. Examples include, but are not limited to, inorganic salts, organic salts, sugars, poly saccharides, polymeric hydrogels, or amphoteric molecules. One preferred material is a hydrogel such as polyvinyl alcohol.

In use, the stent 10 is first positioned in a non-inflated state at the desired site within the body lumen by usual and appropriate delivery means such as an appropriately-sized catheter (not shown). This position is maintained by the delivery means at the site of desired placement for a period of time sufficient to permit the diffusion of an adequate amount of surrounding tissue fluids into the wall 12 to thereby swell the hydrophilic material 32 and inflate the stent 10 so that it independently remains in place by impinging on the interior lumen wall. Of course, the semi-permeable membrane employed to fabricate the wall 12 must be of sufficient strength to resist rupture from the pressure there within created by the expanded hydrophilic material. Ingrowth of tissue eventually occurs through the radial openings 16.

The stent 10 can also be employed as a time-release drug delivery device. In particular, a drug can be disposed with the hydrophilic material 32, either as a separate component or blended therewith. The drug then will be released into the surrounding tissues through the semi-permeable membrane over a period of time. Of course, the drug so included is provided in an appropriate concentration, and may be with a carrier as necessary, to achieve the release rate desired. Additionally, the molecular weight of the drug should be lower than that of the hydrophilic material. One example of such a drug is piroxicam, commercially available as Feldene, manufactured by Pfizer Inc., New York, N.Y., present in an amount of about 20 to 500 mg per stent. The drug can be a separate component, or it can be included within the hydrophilic material by mixing it with or dissolving it into a solution of the hydrophilic material 32 for subsequent timed-release from the stent 10 for therapeutic efficacy. Of course, different drugs can be employed for different stent applications. Non-limiting examples of such drugs include anti-thrombic drugs for cardiovascular applications, anti-calcification drugs for urinary treatment, and anti-inflammatory or growth suppressing drugs for suppression of biologic response to stenting or balloon angioplasty.

The stent 10 can be constructed by providing two concentric tubular membranes whereby the inner surface of the outer membrane and the outer surface of the inner membrane define the inner wall surfaces of the hollow structure. Gel is introduced between the two membranes, after which a membrane sealing process as known in the art seals the ends of the stent 10 and concurrently cuts and seals the radial openings 16.

Figure 2:
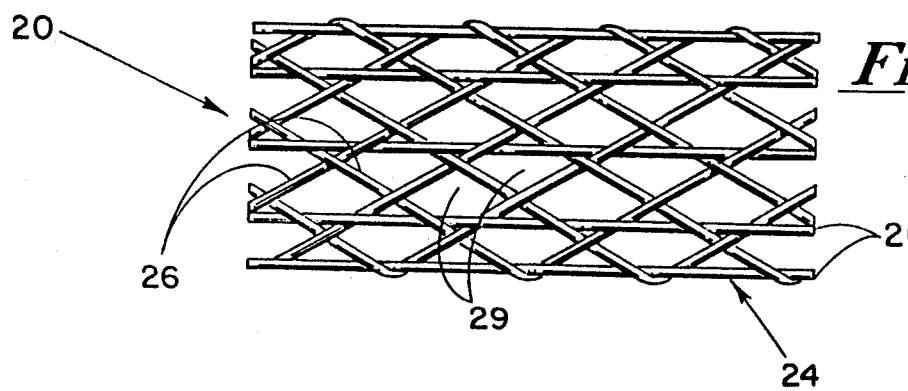
FIG. 2 is an elevation view of a second embodiment of a tubular stent, partially in section, whose entire wall structure is a hollow wall comprising braided inflatable fibers.
Figure 3:
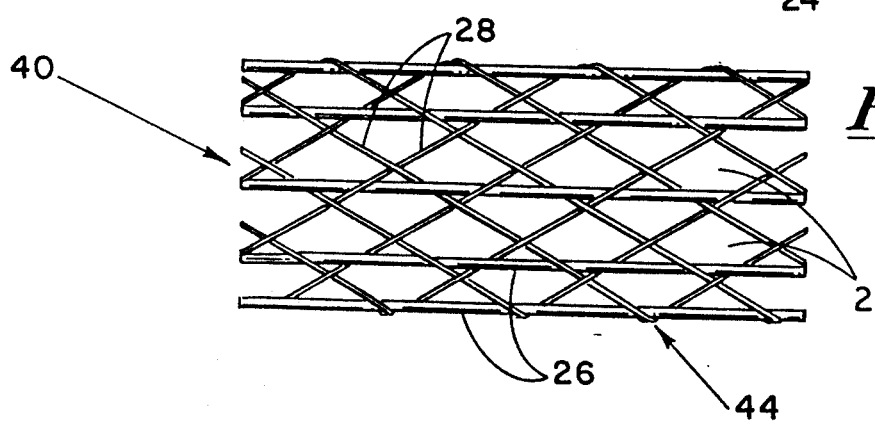
FIG. 3 is an elevation view of a third embodiment of a tubular stent, partially in section, whose wall structure comprises a hollow wall portion of inflatable fibers and a solid wall portion of solid fibers, with both hollow and solid fibers braided together.

FIG. 2 illustrates a second embodiment of a tubular stent 20 for placement within a body lumen. The entire wall structure of the stent 20 is a hollow and inflatable wall 24 comprising a plurality of braided hollow fibers 26. While substantially the entire wall structure can comprise a plurality of braided hollow fibers 26 as shown in FIG. 2, a tubular stent 40 as illustrated in FIG. 3 can be constructed so that only a portion of the wall 44 comprises hollow fibers 26. Thus the hollow fibers 26 of the stent 40 are braided with solid fibers 28. A plurality of radial openings 29 extend through the respective walls 24, 44 to facilitate tissue ingrowth when a stent 20, 40 is in place within a body lumen. As with the balloon 18 of the stent 10 shown in FIG. 1, the hollow fibers 26 of the stent 20, 40 are fabricated of a semi-permeable membrane whose construction is exemplified by polymers that can be formed into semi-permeable membranes as known in the art. Non-limiting examples likewise include polyamides, polyesters, polyurethanes, and ethylene vinyl alcohol. The hollow fibers 26 have disposed therein a hydrophilic material, as described above in relation to FIG. 1, which is capable of absorbing a liquid to thereby increase the volume of the material and accomplish its inflation of the fibers 26. Also, as earlier described, the hydrophilic material can have therewith a drug which will be released into the surrounding tissues through the semi-permeable membrane of the fibers 26 over a period of time.

The stent 20, 40 is positioned as described above in relation to FIG. 1 at its desired site within the lumen. Likewise, this position is maintained by the delivery means at the site of desired placement for a period of time sufficient to permit the diffusion of an adequate amount of surrounding tissue fluids into the fibers 26 to thereby swell the hydrophilic material and inflate the stent 20, 40 so that it independently remains in place by impinging on the interior lumen wall. Of course, the semi-permeable membrane employed to fabricate the hollow fibers 26 must be of sufficient strength to resist rupture from the pressure there within created by the expanded hydrophilic material. Tissue ingrowth occurs through the radial openings 29.

One manner of constructing the stents 20, here described can be employment of solvent casting techniques as known in the art. Thus, for example, an appropriately-shaped die is provided whereby a solution of a polymer is pumped from one portion of the die to form a hollow wall. Simultaneously, a hydrophilic material such as a gel is pumped from another portion of the die central to the polymer solution. When the polymer solution and gel reach a coagulation bath provided in such solvent casting, the gel is surrounded by the polymer as the structure becomes set. Alternatively, of course, the gel can be added under pressure into a length of fiber after which the fiber end is sealed.

Figure 4:
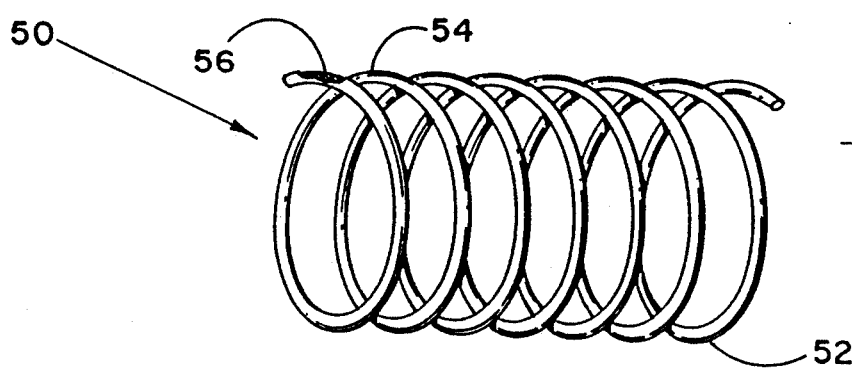
FIG. 4 is a perspective view of a fourth embodiment of a stent, partially in section, whose entire wall structure is a hollow wall comprising an inflatable spiral.

FIG. 4 illustrates a fourth embodiment of a stent 50 whose entire wall structure is a hollow wall 52. In particular, the stent 50 has a hollow and inflatable wall 52 comprising a balloon 54 having a spiral configuration when inflated as shown, yet can be delivered to a site within a lumen in a non-inflated, straightened configuration. As with the stents described in FIGS. 1-4, the wall 52 of the stent 50 is fabricated of a semi-permeable membrane whose construction is exemplified by polymers that can be formed into semi-permeable membranes as known in the art. Non-limiting examples likewise include polyamides, polyesters, polyurethanes, and ethylene vinyl alcohol. The wall 52 has disposed therein a hydrophilic material, as described above in relation to FIG. 1, which is capable of absorbing a liquid to thereby increase the volume of the material and accomplish inflation. At least a portion of the wall 52 can be reinforced with a fiber reinforcement 56 such as a polyester, nylon, or polypropylene, and preferably a polyester. One manner of providing the reinforcement 56 to the wall 52 during manufacture is to braid fibers around the structure and then apply an overcoat of the semi-permeable membrane. Such reinforcement, of course, provides a greater strength to the stent 50.

The hollow wall 52 has disposed therein a hydrophilic material, and the stent 50 is positioned as described above in relation to FIGS. 1-3 at its desired site within the lumen. This position is maintained by the delivery means at the site of desired placement for a period of time sufficient to permit the diffusion of an adequate amount of surrounding tissue fluids into the wall 52 to thereby swell the hydrophilic material and inflate the stent 50 so that it assumes its spiral configuration and independently remains in place by impinging on the interior lumen wall. Of course, the semi-permeable membrane employed to fabricate the inflatable wall 52 must be of sufficient strength to resist rupture from the pressure there within created by the expanded hydrophilic material.

The stent 50 shown in FIG. 4 can also be employed as a time-release drug delivery device. In particular, a drug can be disposed with the hydrophilic material as described above within the wall 52, and will be released into the surrounding tissues through the semi-permeable wall structure over a period of time.

While illustrative and presently preferred embodiments of the invention have been described in detail herein, it is to be understood that the inventive concepts may be otherwise variously embodied and employed and that the appended claims are intended to be construed to include such variations except insofar as limited by the prior art.

What is claimed is:

1. A stent for placement within a body lumen. The stent comprising a wall structure wherein at least a portion thereof is a closed hollow wall having a plurality of radial openings therethrough, fabricated from a semi-permeable membrane, and wherein the hollow wall has disposed therein a hydrophilic material capable of absorbing a liquid to thereby increase the volume of said material.

2. A stent as claimed in claim 1 wherein the hydrophilic material is a gel.

3. A stent as claimed in claim 1 wherein the configuration thereof is tubular.

4. A stent as claimed in claim 3 wherein the stent is a balloon.

5. A stent as claimed in claim 1 wherein the hydrophilic material has disposed therewith a drug.

6. A stent for placement within a body lumen, the stent comprising a wall structure wherein at least a portion thereof is a hollow wall fabricated from hollow closed fibers which are constructed of semi-permeable membranes and held together by being braided, woven or wound together, and wherein the hollow fibers have disposed therein a hydrophilic material capable of absorbing a liquid to thereby increase the volume of said material.

7. A stent as claimed in claim 6 wherein the hydrophilic material is a gel.

8. A stent as claimed in claim 6 wherein the hydrophilic material has disposed therewith a drug.

9. A stent for placement within a body lumen, the stent having a spiral configuration when inflated and comprising a wall structure wherein at least a portion thereof is a closed hollow wall, fabricated from a semi-permeable membrane, and wherein the hollow wall has disposed therein a hydrophilic material capable of absorbing a liquid to thereby increase the volume of said material.

10. A stent as claimed in claim 9 wherein the hydrophilic material has disposed therewith a drug.

11. A stent as claimed in claim 9 wherein at least a portion of the hollow wall is reinforced.

12. A stent as claimed in claim 9 wherein the stent is a balloon.

* * * * *

UNITED STATES PATENT AND TRADEMARK OFFICE
CERTIFICATE OF CORRECTION

PATENT NO.   : 5,234,456
DATED        : August 10, 1993
INVENTOR(S)  : Thomas A. Silvestrini It is certified that error appears in the above-identified patent and that said Letters Patent is hereby corrected as shown below:

Column 5, line 1, delete ".  The" and replace with --, the--;

line 2, add --,-- after "structure";

line 3, add --,-- after "wall";

line 5, delete "." and replace with --,--.

Signed and Sealed this

Twenty-sixth Day of April, 1994

Attest:

BRUCE LEHMAN

*Attesting Officer*     *Commissioner of Patents and Trademarks*